United States Patent [19]

Kuo et al.

[11] Patent Number: 5,180,842
[45] Date of Patent: Jan. 19, 1993

[54] PURIFICATION OF QUINONES

[75] Inventors: Yeong-Jen Kuo; Michael Bellas, both of Kingsport, Tenn.

[73] Assignee: Eastman Kodak Company, Rochester, N.Y.

[21] Appl. No.: 745,774

[22] Filed: Aug. 16, 1991

[51] Int. Cl.$^5$ ............................................. C07C 50/04
[52] U.S. Cl. ................................... 552/293; 552/308; 552/309
[58] Field of Search ........................ 552/308, 309, 293

[56] References Cited
U.S. PATENT DOCUMENTS
3,678,080 7/1972 Crivello ............................ 552/309

Primary Examiner—Marianne Cintins
Assistant Examiner—Kimberly J. Kestler
Attorney, Agent, or Firm—J. Frederick Thomsen; William P. Heath, Jr.

[57] ABSTRACT

Disclosed is a process for removing chlorine-containing impurities from quinone compounds such as p-bezonquinone. The process involves extracting a quinone compound containing 1000 ppm or more chlorine with heptane, cyclohexane or a mixture thereof and separating the quinone compound from the extraction mixture. The process provides a means for obtaining quinone compounds containing 50 ppm or less chlorine.

3 Claims, No Drawings

PURIFICATION OF QUINONES

This invention pertains to a novel process for the purification of quinone compounds. More specifically, this invention pertains to a novel extraction process for the removal of chlorine containing impurities from quinones.

Quinones such as p-benzoquinone, methyl-p-benzo quinone, cyclohexylp-benzoquinone, phenyl-p-benzo quinone, o-benzoquinone, 1,4-aphthoquinone and the like are valuable chemical intermediates useful in the preparation of herbicides, dyes, photographic initiators and the like. p-Benzoquinone also is useful as an inhibitor in processing certain vinyl monomers such as acrylic acid and as a dehydrogenation agent.

Known processes for the manufacture of p-benzoquinone include the oxidation of aniline in the presence of water, sulfuric acid and manganese dioxide. Most of the p-benzoquinone obtained from this process was converted to hydroquinone. U.S. Pat. No. 4,208,339 describes the preparation of p-benzoquinone by the oxidation of phenol with oxygen or an oxygen-containing gas in the presence of cuprous or cupric ions and a second metal such as nickel, iron, tin, cobalt, chromium, molybdenum or magnesium.

Most of the hydroquinone presently manufactured on a commercial scale does not produce p-benzoquinone as an intermediate. Consequently, it has become necessary to develop processes for the conversion of hydroquinone and related compounds to quinone compounds. One classical method for the preparation of p-benzoquinone consists of the oxidation of hydroquinone in the presence of vanadium oxide, sodium chlorate, sulfuric acid and water. See, for example, Organic Sythesis, Vol. II, page 553, 1943, John Wiley and Sons, New York. One disadvantage of this method is it co-produces minor amounts of chlorinated by-products, e.g., chloro-p-benzoquinone and 2,2,-dichloro-4-pentene-1,3-dione, which are extemely difficult to remove from the p-benzoquinone product. For some end uses, the presence of the chlorine-containing impurities in the p-benzoquinone constitutes a significant quality problem. The chlorine also poses corrosion problems in chemical processing equipment in which the chlorine-contaminated p-benzoquinone is utilized.

Extraction or slurry processes are commonly used in the purification of organic chemicals. In such processes, the compound to be purified should exhibit low solubility in the liquid material, i.e., the extractant, employed whereas the impurities should exhibit relatively good solubility in the extractant.

We have discovered that chlorine-containing impurities can be removed selectively from quinone compounds by intimately contacting chlorine-contaminated quinone compounds with heptane, cyclohexane or a mixture thereof at elevated temperature. For example, quinone compounds such as p-benzoquinone containing less than 50 parts per million (ppm) chlorine may be obtained from quinone compounds containing 1000 ppm or greater chlorine with the loss of less than 5 weight percent of the quinone compound in the heptane and/or cyclohexane extractant. The present invention therefore provides a process for obtaining quinone compounds containing less than 50 ppm chlorine which comprises the steps of:

(1) intimately contacting a quinone compound containing at least 1000 ppm chlorine with heptane, cyclohexane or a mixture thereof at elevated temperature; and (2) separating the quinone compound from the mixture of step (1) to obtain the quinone compound containing less than 50 ppm chlorine.

Our purification process may be carried out by agitating a mixture of a chlorine-contaminated quinone compound, in a finely-divided form, with heptane and/or cyclohexane at a temperature of about 25° to 150° C. although the use of temperature in the upper portion of this range may result in excessive loss of the quinone compound. The preferred temperature range therefore is from about 80° to 130° C. The extraction time over which the materials are intimately contacted typically is about 60 to 120 minutes although longer periods of time may be employed. Normally, the amount of heptane and/or cyclohexane extractant used gives an extractant:chlorine-contaminated quinone compound weight ratio of about 1.5:1 to 5:1. The chlorine-depleted quinone compound may be separated from the extraction or slurry mixture by conventional liquid/solid separation techniques such as filtration or centrifugation.

Although our chlorine removal process is especially useful in obtaining p-benzoquinone containing less than 50 ppm chlorine, preferably less than about 20 ppm chlorine, it may be used for purifying substituted benzoquinone compounds. For example, the chlorine-contaminated quinone compounds may be selected from compounds having the general formula

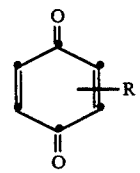

wherein R is hydrogen, alkyl of up to about 8 carbon atoms, halogen, cyclohexyl or phenyl.

The operation of our novel process is further illustrated by the following examples. The examples were carried out by agitating a mixture of various extractants and p-benzoquinone which contained 1300 ppm chlorine in a 250 mL, round bottom flask equipped with a magnetic stirrer and a condenser. Chlorine concentrations were determined by gas/liquid chromatography analysis.

EXAMPLE 1

A mixture of 50 g of the chlorine contaminated p-benzoquinone and 100 mL heptane is agitated at 80° C. for 2 hours. The p-benzoquinone then is collected by filtration and dried. The weight of the recovered p-benzoquinone is 49.3 g (a loss of about 1.5 weight percent). Analysis of a sample of the recovered p-benzoquinone dissolved in acetone showed that the recovered p-benzoquinone contains 14 ppm chlorine.

EXAMPLE 2

Using the procedure described in Example 1, a mixture of 50 g of the chlorine contaminated p-benzoquinone and 100 mL cyclohexane is agitated at 81° C. for 2 hours. The weight of the recovered p-benzoquinone is 48.8 g (a loss of about 3 weight percent) and its chlorine content is 4 ppm.

The following comparative examples show that extractants other than heptane and cyclohexane are not as effective in removing chlorine containing contaminants and/or result in the loss of significantly greater amounts of p-benzoquinone. These examples were carried out at the boiling points of the extractants used.

COMPARATIVE EXAMPLE 1

Using the procedure described in Example 1, a mixture of 50 g of the chlorine contaminated p-benzoquinone and 100 mL pentane is agitated at 35° C. for 2 hours. The weight of the recovered p-benzoquinone is 49.2 g (a loss of about 1.6 weight percent) and its chlorine content is 150 ppm.

COMPARATIVE EXAMPLE 2

Using the procedure described in Example 1, a mixture of 50 g of the chlorine-contaminated p-benzoquinone and 100 mL hexane is agitated at 69° C. for 2 hours. The weight of the recovered p-benzoquinone is 48.8 g (a loss of about 3 weight percent) and its chlorine content is 124 ppm.

COMPARATIVE EXAMPLE 3

Using the procedure described in Example 1, a mixture of 25 g of the chlorine-contaminated p-benzoquinone and 100 mL water is agitated at 25° C. for 2 hours. The weight of the recovered p-benzoquinone is 24.2 g (a loss of about 3 weight percent) and its chlorine content is 172 ppm.

COMPARATIVE EXAMPLE 4

Using the procedure described in Example 1, a mixture of 50 g of the chlorine-contaminated p-benzoquinone and 100 mL isobutyl acetate is agitated at 115° C. for 2 hours. The weight of the recovered p-benzoquinone is 40 g (a loss of about 20 weight percent) and its chlorine content is 37 ppm.

COMPARATIVE EXAMPLE 5

Using the procedure described in Example 1, a mixture of 50 g of the chlorine contaminated p-benzo quinone and 100 mL octane is agitated at 126° C. for 2 hours. The weight of the recovered p-benzoquinone is 46.2 g (a loss of about 7.6 weight percent) and its chlorine content is 40 ppm.

The invention has been described in detail with particular reference to preferred embodiments thereof, but it will be understood that variations and modifications may be effected within the spirit and scope of the invention.

We claim:

1. Process for obtaining a quinone compound containing less than 50 ppm chlorine which comprises the steps of:
   (1) intimately contacting a quinone compound containing at least 1000 ppm chlorine with heptane, cyclohexane or a mixture thereof at elevated temperature; and
   (2) separating the quinone compound from the mixture of step (1) to obtain the quinone compound containing less than 50 ppm chlorine.

2. Process according to claim 1 wherein the quinone is selected from compounds having the general formula

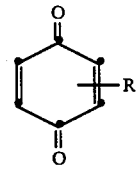

wherein R is hydrogen, alkyl of up to about 8 carbon atoms, halogen, cyclohexyl or phenyl and step (1) is carried out at a temperature of about 80° to 130° C. and the weight ratio of the heptane, cyclohexane or mixture thereof to the quinone compound is about 1.5:1 to 5:1.

3. Process for obtaining p-benzoquinone containing less than 20 ppm chlorine which comprises the steps of:
   (1) intimately contacting p-benzoquinone containing at least 1000 ppm chlorine with heptane, cyclohexane or a mixture thereof at a temperature of about 80° to 130° C. wherein the weight ratio of the heptane, cyclohexane or mixture thereof to p-benzoquinone is about 1 5:1 to 5:1; and
   (2) separating p-benzoquinone from the mixture of step (1) to obtain p-benzoquinone containing less than 20 ppm chlorine.

* * * * *

UNITED STATES PATENT AND TRADEMARK OFFICE
CERTIFICATE OF CORRECTION

PATENT NO. : 5,180,842

DATED : January 19, 1993

INVENTOR(S) : Yeong-Jen Kuo et al.

It is certified that error appears in the above-identified patent and that said Letters Patent is hereby corrected as shown below:

Column 4, line 14 (Claim 1, line 8), between "(2) separating" and "the", --- by filtration or centrifugation --- should be inserted.

Signed and Sealed this

Twenty-sixth Day of October, 1993

Attest:

BRUCE LEHMAN

Attesting Officer

Commissioner of Patents and Trademarks